Feb. 26, 1957 M. G. LAFKY Plant Pat. 1,569

IRIS PLANT

Filed Nov. 28, 1955

WITNESS

Gadison E. Avery

INVENTOR

MARK G. LAFKY by Rummler, Rummler & Snow

ATTYS.

United States Patent Office

Plant Pat. 1,569

Patented Feb. 26, 1957

1,569

IRIS PLANT

Mark G. Lafky, Sherwood, Oreg.

Application November 28, 1955, Serial No. 549,580

1 Claim. (Cl. 47—60)

Figures 1, 2, 3, 4:
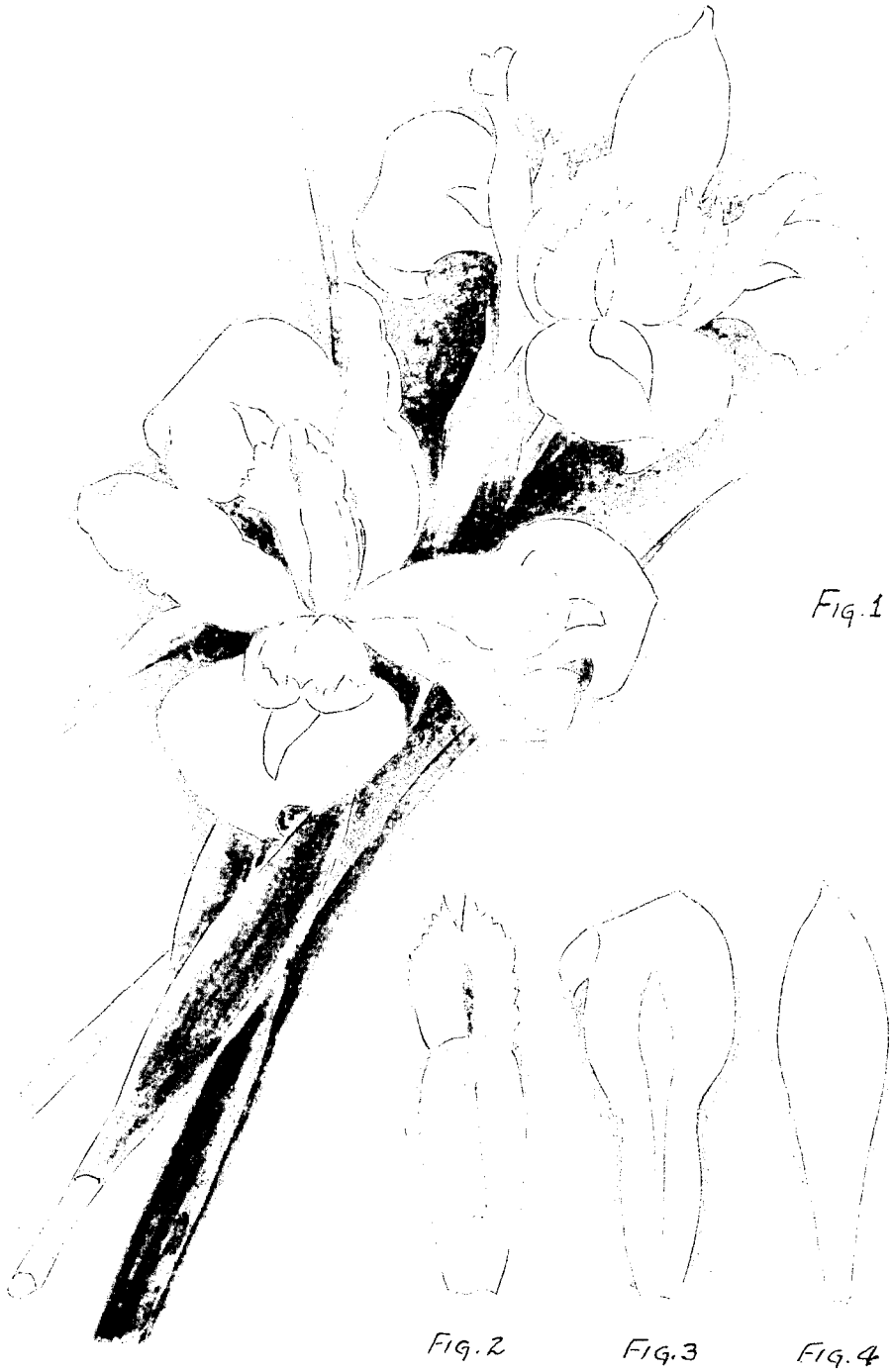

The present discovery relates to a new and distinct variety of white iris plant which originated as a sport of the well-known variety "Wedgewood" blue iris, unpatented. The new sport was discovered by me in my nursery at Sherwood, Oregon, in 1940, among cultivated plants of the blue "Wedgewood."

My new variety of iris has been found to hold its distinguishing characteristics through succeeding generations by the natural increase of the bulbs or root stock, grown at Sherwood, Oregon, since the white sport was discovered.

The primary object in carrying out this invention was to establish the distinctive white color of its flowers in combination with the size, form, very vigorous growth and good forcing qualities of its parent "Wedgewood." At the present time white and yellow varieties of iris do not force as well or as early as "Wedgewood."

In general the plant form and structure of my new variety is like the parent "Wedgewood" blue iris and particularly is similar to the Tingitana species of the Xiphium bulbous iris group, having stout erect stems, sword-shaped and overlapped leaves, and flowers with three large white outer petals alternating with narrower blade-like white outer petals. The large outer petals have a relatively narrow orange-yellow beard extending down the mid rib and each is overlaid by a narrow inner petal having a double claw-like tip end which inner petal has a central channel-like formation on its bottom side along which a single pale yellow stamen extends. Each of the large outer petals terminates in a claw-like tip which curves downwardly and inwardly toward the base of the flower.

The accompanying illustrations show in Fig. 1 a cluster of flowers and leaves in full color, and below, pen and ink sketches of the three types of petals that are contained in the bloom; Fig. 2 being an under-side view of one of the innermost petals which has a central channel-like formation behind which a single stamen is located as shown; Fig. 3 being an inner or top-side view of one of the large outer petals; and Fig. 4 being a plan view of one of the blade-like outer petals which alternate with the petals of Fig. 3.

The color designations for the new variety as shown, according to "A Dictionary of Color" by Maerz and Paul, are as follows:

| | Plate | Letter | No. |
|---|---|---|---|
| *Flower* | | | |
| Main color white: | | | |
| From | 9 | A | 1 |
| To | 9 | B | 1 |
| Yellow center stripe or beard on large white petals as shown in Figs. 1 and 3: | | | |
| From | 9 | L | 1 |
| To | 9 | L | 6 |
| Single stamen as shown in Fig. 2—pale creamy yellow on white stem | 9 | B | 3 |
| *Leaves* | | | |
| Main leaf—green: | | | |
| From | 20 | L | 6 |
| To | 22 | K | 7 |

The variety which this new white iris most resembles is its parent plant, "Wedgewood" blue iris. "Wedgewood" blue iris constitutes 90% of the forced iris on the December, January and February flower markets and is noted for its full and large size, its hardy growth and its excellent forcing qualities. White and yellow iris are greatly in demand but those heretofore known do not force as early nor as well as "Wedgewood" blue variety.

My new variety of white iris, however, is essentially like its parent in size and form, with the same vigorous growth, large flowers, good forcing qualities and early blooming period, all of which combine to make it a good commercial product.

Both the parent blue "Wedgewood" iris and this white sport are sterile in ovaries and pollen and cannot be used for breeding.

Like its parent my new variety blooms once, normally in the early spring, and the main distinction of the new variety lies in the large white flowers that it produces.

Having thus disclosed the invention, I claim:

A new and ornamental variety of white iris plant of the Tingitana strain particularly characterized as to novelty by its large pure white blooms, the bright yellow colored beard running down the center of the three large outer petals of each flower, its early blooming period, and its good forcing qualities.

No references cited.